United States Patent
Lynnworth

(10) Patent No.: US 7,481,114 B2
(45) Date of Patent: Jan. 27, 2009

(54) NONINVASIVE MEASUREMENT OF FLUID CHARACTERISTICS USING REVERSIBLY DEFORMED CONDUIT

(76) Inventor: Lawrence C. Lynnworth, 77 Graymore Rd., Waltham, MA (US) 02451-2201

( * ) Notice: Subject to any disclaimer, the term of this patent is extended or adjusted under 35 U.S.C. 154(b) by 287 days.

(21) Appl. No.: 11/486,138

(22) Filed: Jul. 13, 2006

(65) Prior Publication Data

US 2008/0011060 A1    Jan. 17, 2008

(51) Int. Cl.
G01N 29/024 (2006.01)
G01F 1/66 (2006.01)

(52) U.S. Cl. ...................... 73/597; 73/861.27

(58) Field of Classification Search .............. 73/597, 73/861.18, 861.27–861.31
See application file for complete search history.

(56) References Cited

U.S. PATENT DOCUMENTS

| | | | |
|---|---|---|---|
| 3,575,050 A | 4/1971 | Lynnworth | 166/281 |
| 3,731,532 A | 5/1973 | Courty | 73/861.03 |
| 3,906,791 A | 9/1975 | Lynnworth | 73/861.29 |
| 3,921,622 A * | 11/1975 | Cole | 600/437 |
| 4,195,517 A | 4/1980 | Kalinoski et al. | 73/194 A |
| 4,397,194 A | 8/1983 | Soltz | 73/861.28 |
| 4,722,224 A * | 2/1988 | Scheller et al. | 73/599 |
| 5,006,266 A * | 4/1991 | Schram | 210/748 |
| 5,179,862 A | 1/1993 | Lynnworth | 73/861.28 |
| 5,394,732 A * | 3/1995 | Johnson et al. | 73/19.1 |
| 5,629,681 A * | 5/1997 | DuVall et al. | 340/665 |
| 6,065,350 A | 5/2000 | Hill et al. | 73/861.27 |
| 6,330,831 B1 | 12/2001 | Lynnworth et al. | 73/861.28 |
| 6,418,796 B1 * | 7/2002 | Baumoel | 73/861.28 |
| 7,194,919 B2 * | 3/2007 | Shkarlet et al. | 73/861.18 |
| 2006/0052963 A1 * | 3/2006 | Shkarlet | 702/108 |

OTHER PUBLICATIONS

Johner, C. Chamney, P., Schneditz, D. and Kramer, M. 1998 Nephrol. Dial. Transplant 13:2098-2103 Evaluation of an ultrasonic blood volume monitor.

* cited by examiner

Primary Examiner—Hezron Williams
Assistant Examiner—Rose M Miller
(74) Attorney, Agent, or Firm—Joyce E. Lauer

(57) ABSTRACT

An apparatus for determining a characteristic for a fluid in a tube, the apparatus including a force applying system to cause a change in a transverse dimension of a segment of the tube, wherein the change in the transverse dimension is reversible, and an ultrasonic system that comprises a single transducer for launching and receiving ultrasonic signals. Ultrasonic signals propagate through the tube along colinear paths of different lengths that are orthogonal to the tube wall. At least one of the paths is located entirely within the segment. Each of the ultrasonic signals propagates through the tube wall in a first wall region and reflects from an inner surface of a second wall region. Path length differences between the paths are determined, and transit times are determined for each of the ultrasonic signals. The characteristic is determined based on information including the path length differences and the transit times.

9 Claims, 10 Drawing Sheets

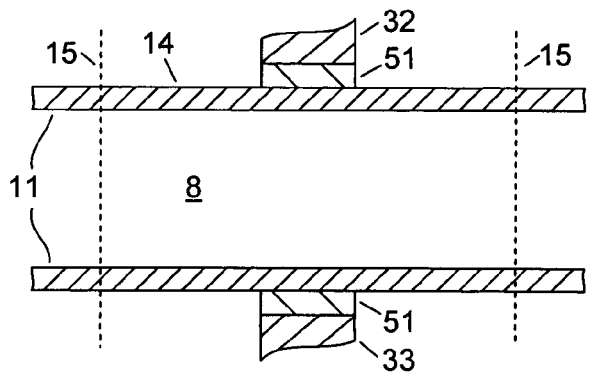
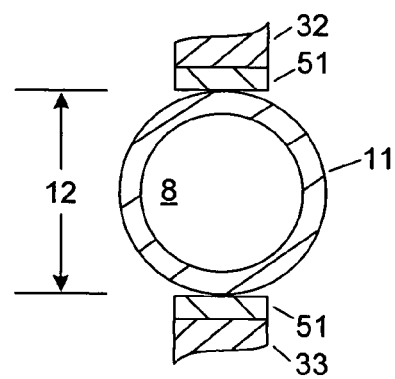
FIG. 2A  FIG. 2B
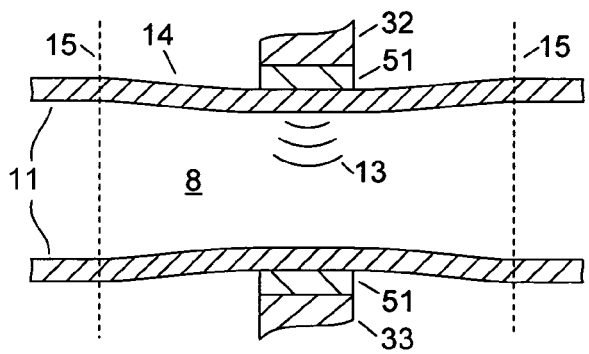
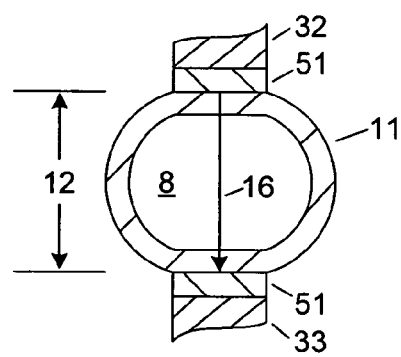
FIG. 2C  FIG. 2D
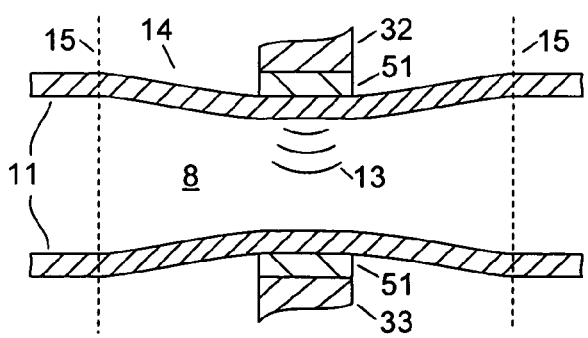
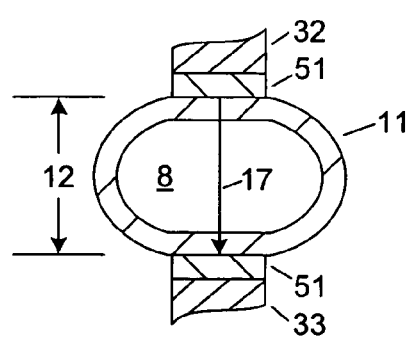
FIG. 2E  FIG. 2F

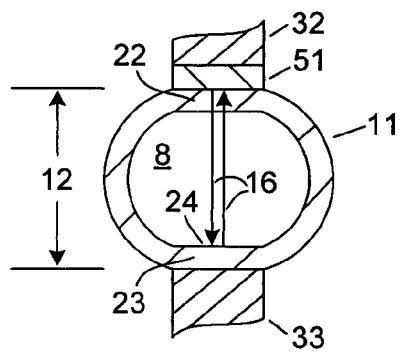
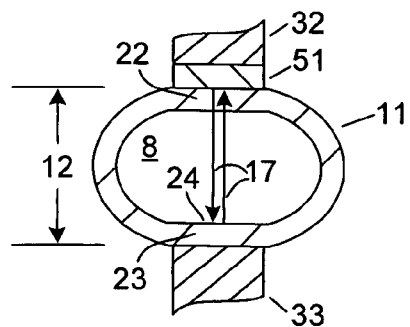
FIG. 4A   FIG. 4B
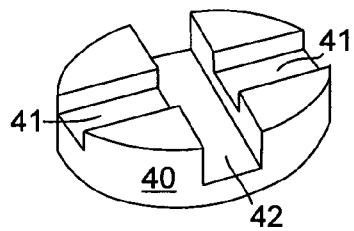
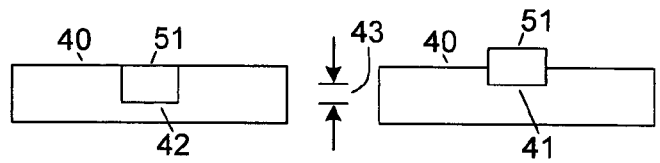
FIG. 5A   FIG. 5B   FIG. 5C
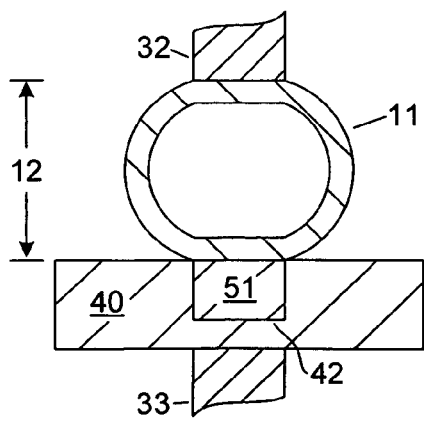
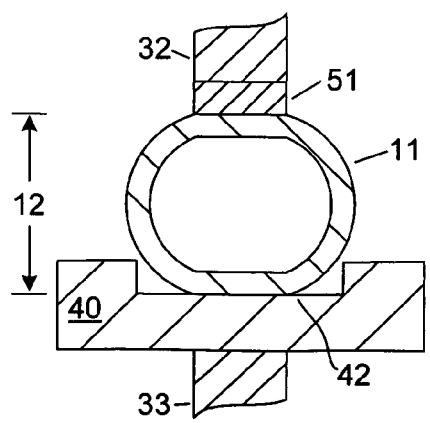
FIG. 5D   FIG. 5E

NONINVASIVE MEASUREMENT OF FLUID CHARACTERISTICS USING REVERSIBLY DEFORMED CONDUIT

BACKGROUND

Embodiments described herein relate to accurate determination of sound speed, or of other characteristics derivable from sound speed, for a fluid in a conduit or tube. Characteristics derivable from sound speed include characteristics such as: fluid density, composition, purity, and temperature; the concentration of component A in a binary fluid mixture of A and B; and total protein concentration in a fluid such as blood. The fluid of interest may be flowing or at rest. Fluid sound speed typically is determined by launching an ultrasonic signal that propagates through a fluid along a path of known length, receiving the signal after it has propagated, and calculating the sound speed based on the path length and the time elapsed between launching and receiving of the signal. The ultrasonic signal may be launched and received using one or more transducers.

Sound speed includes a real part represented by the symbol c, which is typically expressed in units of m/sec. Sound speed also includes an imaginary part that is related to energy absorption processes, and which is described by an attenuation coefficient that is typically expressed in units of dB/cm. Sound speed is influenced by composition, temperature, pressure, and other variables or characteristics of the fluid. In liquids, for example, c is inversely proportional to the square root of the product of compressibility and density; thus any factor that affects compressibility or density may change the sound speed. In gases, c is inversely proportional to the square root of the molecular weight of the gas. In gases, c is directly proportional to the square root of temperature and of gamma, where gamma is the ratio of specific heat at constant pressure to specific heat at constant volume.

Using known relationships between sound speed and other variables or characteristics, sound speed measurements can lead to determination of values for the other variables or characteristics. Sound speed measurements alone cannot solve a multivariable problem, however. Even for a simple fluid such as pure water, measuring sound speed yields a unique value for a variable such as temperature only if the temperature is within a certain range and if the pressure is known. Viewed in another way, one challenge in measuring sound speed is to eliminate interfering variables. Another challenge is to measure sound speed accurately; for example, to measure c with an error of less than 0.1 percent, or to measure the attenuation coefficient with an error of less than 1 percent.

Fluid sound speed is sometimes determined using contrapropagation; this technique is typically used in a situation where the fluid is flowing. Ultrasonic signals are launched in opposite directions along two paths that, in the absence of flow, would be congruent, i.e. in exactly the same position and of equal length. Sound speed may be determined as the average of the speed along the two paths. Contrapropagation systems often try to employ long axial paths, as described in U.S. Pat. No. 5,179,862 and U.S. Pat. No. 6,065,350. In the '862 and '350 systems, the transducers are positioned external to the tube wall, so the paths traverse one or more regions of tube wall in addition to traversing the fluid of interest, and the differing sound speeds in the wall and the fluid can complicate the accurate determination of fluid sound speed. The total path length in the '862 and '350 systems is very long, so the wall path length is a small fraction of the total path length, and in practice the error introduced by the wall path length is sometimes ignored in long axial path systems.

In some situations, a long axial path may be impractical. For example, the tube may be positioned within a confined space that provides access to only a small axial portion of the tube. In such situations, it may be advantageous to employ a path that is orthogonal or oblique to the tube wall. For a path that is orthogonal or oblique to the tube wall, with transducers positioned external to the tube wall, the wall path length may be a significant fraction of the total path length, leading to problems in accurately determining fluid path length and fluid sound speed. U.S. Pat. Nos. 3,731,532 and 4,397,194 employ externally-positioned transducers and paths that are oblique or orthogonal to the tube wall. In the '532 apparatus, fluid sound speed is measured along one fixed path orthogonal to the tube. In the '194 apparatus, measurement of the transit time in the fluid along one fixed path orthogonal to the tube wall is interpreted in terms of tube inside diameter, assuming a known fluid sound speed. The '532 apparatus and the '194 apparatus use oblique paths to measure flow effects on transit times, from which the flow velocity is determined.

Ultrasonic determination of sound speed may use differential paths, which are paths whose lengths differ. Differential paths may help to determine sound speed accurately; multiple determinations along fluid paths of differing lengths provide information about linearity and consistency of the determinations. For example, ultrasonic determinations of fluid properties may use a flowcell or spool that includes one or more transducers, the spool being inserted into a tube or conduit containing a fluid of interest, and the transducers may be positioned on the flowcell to launch and receive signals along differential paths.

It is possible to determine fluid sound speed by penetrating a tube wall with one or more ports and positioning one or more transducers in direct contact with the fluid. This technique removes the inaccuracy caused by wall path contributions, but the technique is invasive: the fluid may become contaminated, and the transducer in contact with the fluid may disturb the flow or may cause debris to accumulate. A less-invasive technique is to use a flowcell that has no ports. Installation of the flowcell requires, for example, provision of a flanged opening of length equal to the flowcell's length or cutting of the tube wall to install the flowcell. Junctions between gasketed mating flanges or between the flowcell and the tube wall may cause problems because of seemingly minor misalignment or diameter mismatch.

A noninvasive technique for determining fluid sound speed may be advantageous in some settings, such as where the fluid-containing tube is part of a biomedical device or a semiconductor processing system. In such settings, it may be important to prevent contamination of the fluid and to maintain sterility of the fluid. In addition, it may be important to avoid any irregularity in the inner surface of the tube wall that might encourage accumulation of debris or, in the case of blood processing equipment, blood clot formation. A noninvasive apparatus may be defined as a system in which there is no penetration of the tube wall during installation or use of the fluid sound speed measuring apparatus. The systems described in the '862 and '350 patents are noninvasive, but each uses a long axial path, as noted above.

There is a need for a fluid sound speed determination system or method that is noninvasive and that eliminates unknown contributions from portions of the system that are external to the fluid of interest.

SUMMARY

An apparatus for determining a characteristic such as sound speed for a fluid in a tube comprises means for applying a force to cause a change in a transverse dimension of a segment of the tube, wherein the change in the transverse dimension is reversible, and means for launching and receiving ultrasonic signals. Ultrasonic signals propagate through the tube along paths of different lengths. At least one of the paths is located entirely within the segment having the changed transverse dimension. The applied force may cause the transverse dimension to change continuously or in discrete steps. Path length differences between the paths are determined, and transit times are determined for each of the ultrasonic signals. The characteristic is determined based on information comprising the path length differences and the transit times.

BRIEF DESCRIPTION OF THE DRAWINGS

FIGS. 2A, 2C and 2E are longitudinal-section views of a portion of the apparatus and tube of FIG. 1A, with the plane of section taken along line AA of FIG. 1B; the deformation of the tube differs in FIGS. 2A, 2C and 2E.

FIGS. 2B, 2D and 2F are cross-sectional views of a portion of the apparatus and tube of FIG. 1A, with the plane of section taken along line BB of FIG. 1A; the deformation of the tube differs in FIGS. 2B, 2D and 2F.

FIGS. 4A and 4B are cross-sectional views of a portion of an apparatus and tube, the apparatus including a single transducer 51, in accordance with another embodiment; the deformation of the tube differs in FIGS. 4A and 4B.

FIG. 5A is a perspective view of a spacer 40 having two grooves 41 and 42 that differ in depth, the two grooves being oriented perpendicular to one another.

FIGS. 5B and 5C are side views of the spacer of FIG. 5A; in FIG. 5B the spacer is viewed from one end of groove 42, and in FIG. 5C the spacer is viewed from one end of groove 41.

FIG. 5D is a cross-sectional view of a portion of an apparatus and tube, the apparatus including a spacer 40 adjacent a spindle 33, with a transducer 51 fitted into groove 42, in accordance with another embodiment.

FIG. 5E is a cross-sectional view of a portion of an apparatus and tube, the apparatus including a spacer 40 adjacent a spindle 33, the tube compressed against groove 42, in accordance with another embodiment.

DETAILED DESCRIPTION

Reference will now be made in detail to some embodiments, examples of which are illustrated in the accompanying drawings.

Figure 1A:
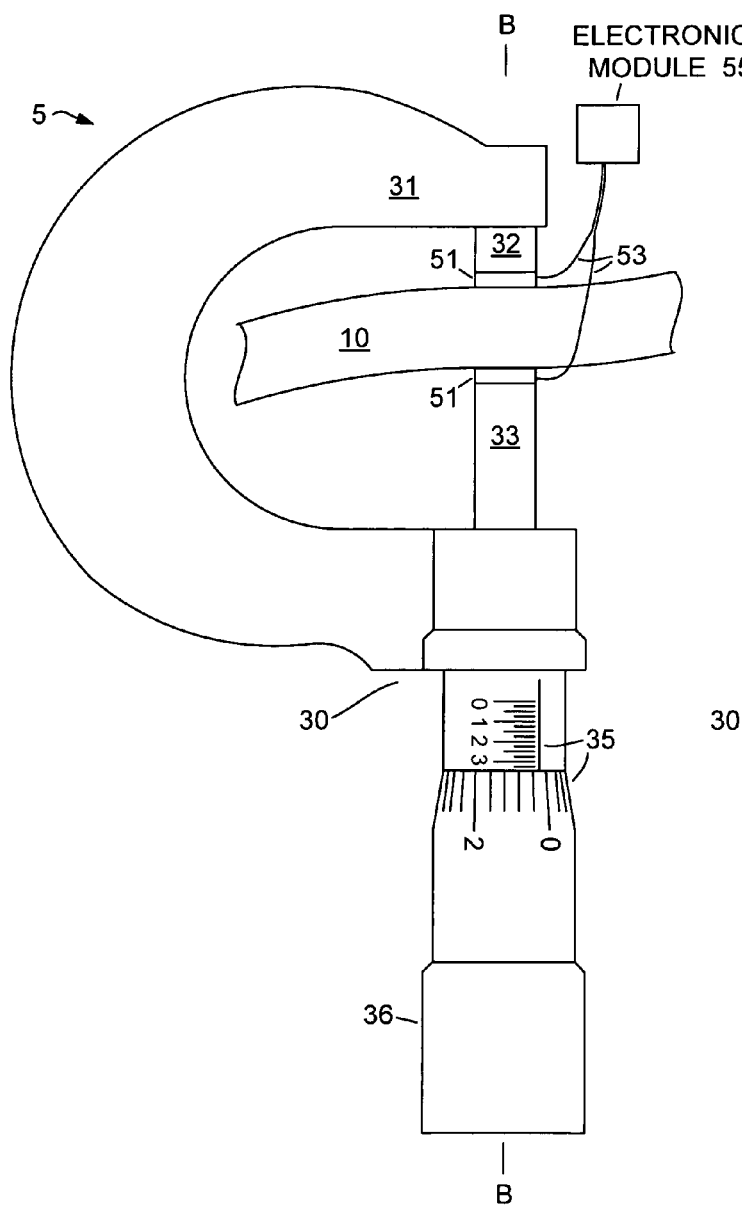
FIG. 1A is a side view of an apparatus for determining a characteristic of a fluid in a tube, in accordance with one embodiment.
Figure 1B:
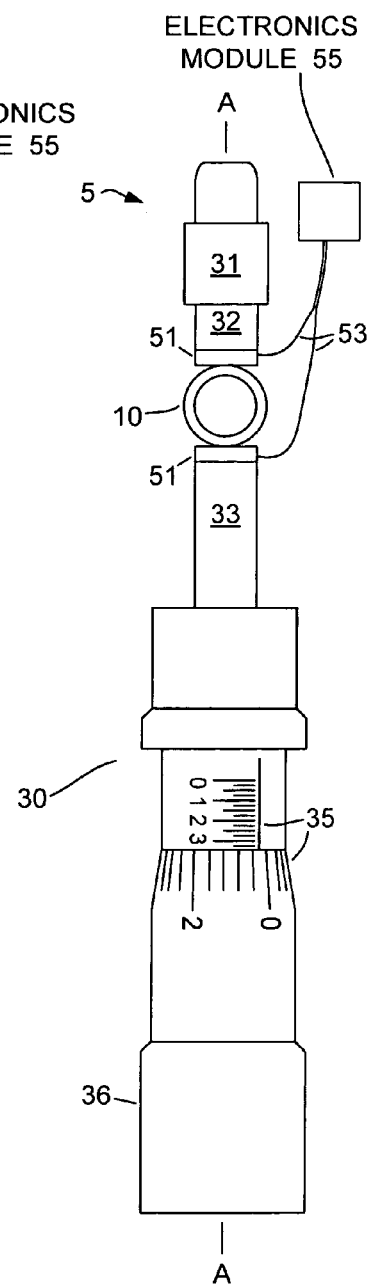
FIG. 1B is a side view of the apparatus and tube of FIG. 1A after rotation of the apparatus about axis BB of FIG. 1A.

FIG. 1A is a side view of an apparatus 5 for determining a characteristic of a fluid in a tube 10, in accordance with one embodiment. Apparatus 5 includes a conventional micrometer 30 and two transducers 51 that are coupled to electronics module 55 by electrical leads 53. Each transducer 51 is capable of launching and receiving ultrasonic signals, as is known in the art. Electronics module 55 includes transmitter and receiver means and also includes means for echo selection, echo rejection, filtering, gain adjustment and timing, as is known in the art. Micrometer 30 includes a C-shaped frame 31, an anvil 32, a spindle 33, a scale 35, and a barrel 36. One transducer 51 is attached to anvil 32, and the other transducer 51 is attached to spindle 33. Tube 10 is held between the two transducers 51. For clarity, FIG. 1A depicts only a truncated portion of tube 10. Tube 10 contains a fluid, which may be a liquid, a gas, or a multiphase mixture; the fluid may be flowing or at rest. FIG. 1B is a side view of the apparatus and tube of FIG. 1A after rotation of the apparatus about axis BB of FIG. 1A.

Spindle 33 and anvil 32 together apply a force which holds transducers 51 against tube 10. Spindle 33 may be advanced so that it moves closer to anvil 32, causing the distance between the two transducers 51 to decrease. Alternatively, spindle 33 may be retracted, causing the distance between the two transducers 51 to increase. If spindle 33 is advanced, the force applied by spindle 33 and anvil 32 may cause a change in a transverse dimension of a segment of tube 10; in other words, a segment of tube 10 may be temporarily deformed. If spindle 33 is then retracted, thereby changing the applied force, the deformation of the segment may be reversed. Reversible deformation of tube 10 may be used to change the length of a path for an ultrasonic signal that is propagated from one transducer 51 to the other transducer 51. Paths of different length (differential paths) may facilitate accurate determination of sound speed for a fluid within tube 10. Differential deformations of tube 10 may be used to generate differential paths, as described further below.

FIG. 2A is a longitudinal-section view of a portion of the apparatus and tube of FIG. 1A, with the plane of section taken along line AA of FIG. 1B. Tube 10 includes a tube wall 11 and a segment 14, the segment being delimited by segment boundaries 15. Segment boundaries 15 do not correspond to physical elements, but simply aid in depicting segment 14. Segment 14 is described further in connection with FIGS. 2C-D. Tube 10 contains a fluid 8. Transducers 51 are held against tube wall 11 by anvil 32 and spindle 33. FIG. 2B is a cross-sectional view of a portion of the apparatus and tube of FIG. 1A, with the plane of section taken along line BB of FIG. 1A. The portion depicted in FIG. 2B is the same as that depicted in FIG. 2A. A transverse dimension 12 for segment 14 of tube 10 is indicated in FIG. 2B. Transverse dimension 12 may be determined by reading scale 35 of micrometer 30.

FIG. 2C is similar to FIG. 2A, except that in FIG. 2C spindle 33 has advanced, reducing the distance between transducers 51 and compressing segment 14 of tube 10. FIG. 2D is similar to FIG. 2B. Transverse dimension 12 in FIG. 2D is smaller than transverse dimension 12 in FIG. 2B, because the force applied by spindle 33 and anvil 32 has compressed segment 14. Segment 14 is understood to be the portion of tube 10 whose transverse dimension 12 is changed as a result of the application of force by spindle 33 and anvil 32. Transverse dimension 12 may be determined by reading scale 35 of micrometer 30. In FIG. 2C, one transducer 51 launches an ultrasonic signal 13. Ultrasonic signal 13 propagates along path 16 of FIG. 2D and is received at the other transducer 51. Ultrasonic signal 13 propagates through tube wall 11 adjacent the launching transducer 51, then through fluid 8, and then through tube wall 11 adjacent the receiving transducer 51. Each transducer 51 is coupled to electronics module 55 by electrical leads 53, as shown in FIGS. 1A and 1B. The transit time of ultrasonic signal 13 along path 16 may be determined by the two transducers 51 and electronics module 55, as is known in the art.

FIG. 2E is similar to FIG. 2C, except that in FIG. 2E spindle 33 has advanced further, thus further reducing the distance between transducers 51 and further compressing segment 14 of tube 10. FIG. 2F is similar to FIG. 2D. Transverse dimension 12 in FIG. 2F is smaller than transverse dimension 12 in FIG. 2D, because of the further compression of segment 14. Transverse dimension 12 may be determined by reading scale 35 of micrometer 30. In FIG. 2E, one transducer 51 launches an ultrasonic signal 13. Ultrasonic signal 13 propagates along path 17 of FIG. 2D and is received at the other transducer 51. Ultrasonic signal 13 propagates through tube wall 11 adjacent the launching transducer 51, then through fluid 8, and then through tube wall 11 adjacent the receiving transducer 51. The transit time of ultrasonic signal 13 along path 17 may be determined by the two transducers 51 and electronics module 55, as is known in the art.

The path length for path 16 is substantially equal to the transverse dimension 12 depicted in FIG. 2D. The path length for path 17 is substantially equal to the transverse dimension 12 depicted in FIG. 2F. The path length for path 17 is smaller than the path length for path 16. The path length difference is defined to be a difference between the path lengths for two paths of differing length, such as path 16 and path 17. In this embodiment, the path length difference is substantially equal to the change in the transverse dimension 12 from FIG. 2D to FIG. 2F. The path length within tube wall 11 is assumed to be the same for path 16 and path 17, but the path length within fluid 8 (the fluid path length) differs for path 16 and path 17. Thus, a difference in the fluid path length for path 16 and path 17 corresponds to the path length difference, which is substantially equal to the change in transverse dimension 12 from FIG. 2D to FIG. 2F. The transverse dimension 12 determined for segment 14 of FIG. 2F may be subtracted from the transverse dimension 12 determined for segment 14 of FIG. 2D to yield the change in transverse dimension 12.

Figure 3:
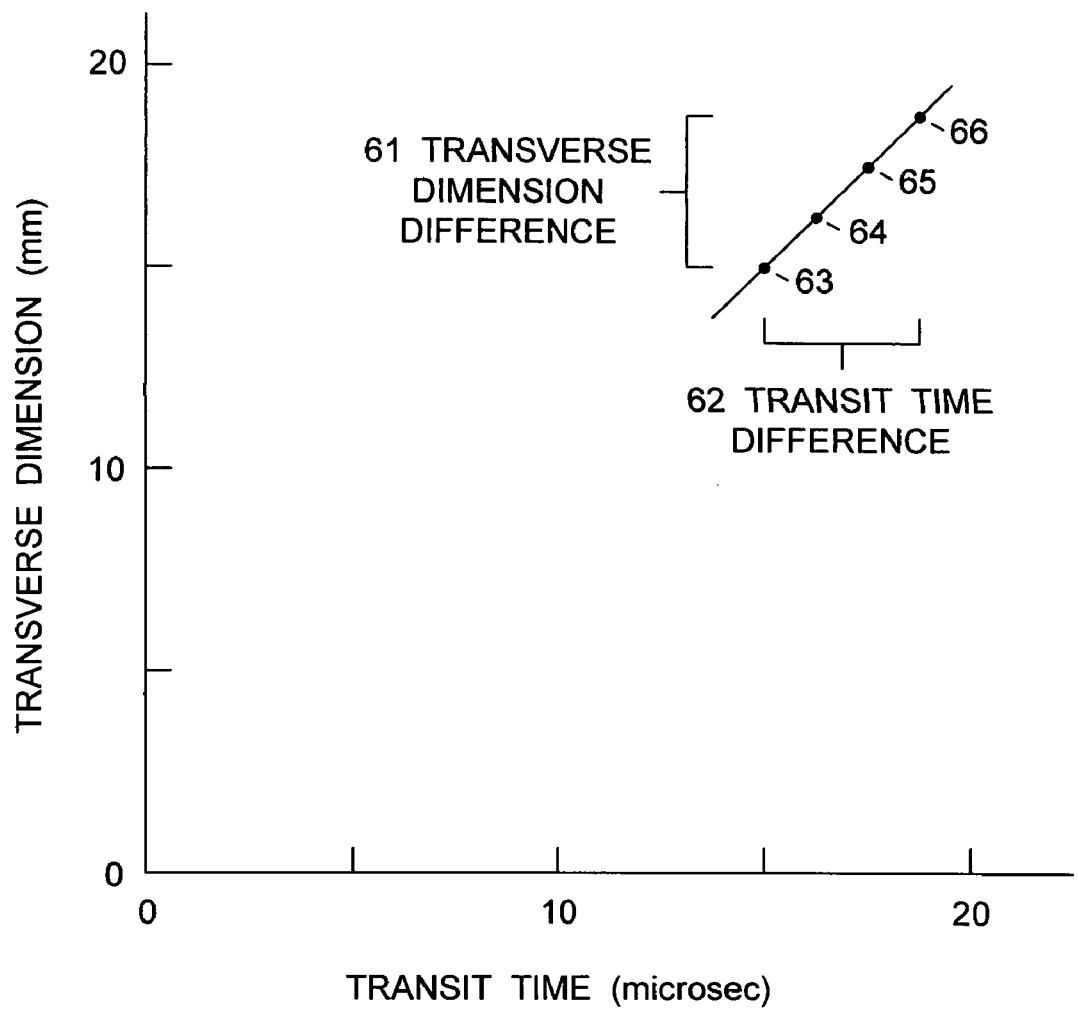
FIG. 3 is an example of a graph that plots the transit time of an ultrasonic signal propagated in a tube as a function of the transverse dimension of the tube.

FIG. 3 is an example of a graph that plots the transit time of an ultrasonic signal 13 propagated in a tube 10 as a function of the transverse dimension 12 of the tube. Points 63-66 represent idealized hypothetical values for a tube 10 subjected to four different levels of applied force resulting in four different transverse dimensions 12. Point 66 has the largest value for the transverse dimension 12 and the largest value for the transit time, while point 63 has the smallest value for the transverse dimension 12 and the smallest value for the transit time.

The transverse dimension difference 61 depicted in FIG. 3 is qualitatively analogous to the change in transverse dimension 12 from FIG. 2D to FIG. 2F which, as noted above, equals the difference in fluid path length. The transit time difference 62 depicted in FIG. 3 is qualitatively analogous to a difference between the transit times determined for paths 16 and 17 in FIGS. 2D and 2F. Dividing the transverse dimension difference 61 by the transit time difference 62 yields the sound speed in fluid 8 (fluid sound speed). In other words, the fluid sound speed equals the slope of a line that passes through points 63 and 66. Thus, reversible deformation of tube 10 can facilitate an accurate determination of a characteristic such as fluid sound speed, based on information comprising the path length difference and the transit times. This determination is independent of knowledge of the thickness or properties of tube wall 11. In the embodiment of FIG. 2A-F, where the absolute path lengths are known from the transverse dimensions 12, determination of the characteristic may be based upon information comprising the two path lengths and the two transit times.

Two or more differential paths may be employed for determination of sound speed. For simplicity of description, many of the figures included herein depict only two differential paths. In practice, it may be advantageous to employ a larger number of differential paths. While it is possible to determine a characteristic such as sound speed using only two points 63 and 66, more accurate determination may be achieved based on information that includes additional pairs of values for transverse dimension 12 and transit time, as indicated by points 64 and 65. Using multiple value pairs (points), multiple path length differences and transit time differences may be determined and used to determine a more accurate value for a characteristic such as sound speed. In other words, multiple value pairs (points) may be used to determine the best fit for a line whose slope represents sound speed. To obtain a large number of value pairs, spindle 33 may be repositioned (advanced or retracted) progressively, thereby changing transverse dimension 12 of segment 14 progressively, while transverse dimension 12 and transit time are recorded repeatedly as spindle 33 is repositioned. The repositioning of spindle 33 may be discrete (stepwise) or continuous, causing transverse dimension 12 to change in discrete steps or to change continuously; the repositioning may be partly discrete and partly continuous. In discrete mode, for example, spindle 33 may be repositioned in 1000 increments of 0.0001 inch each, for a total displacement of 0.1 inch. In continuous mode, for example, spindle 33 may be advanced continuously for a total displacement of 0.1 inch.

Repositioning of spindle 33 or of another urging member that applies force to segment 14 may be accomplished manually or by automatic means. Automatic means for repositioning may comprise a small motor, a stepper motor, or any of various linear or rotary actuator devices, as is known in the art. In one embodiment, suitable for either discrete or continuous mode, application of force to change transverse dimension 12 may be accomplished using a datum frame plus a linear actuator device; the linear actuator device may be coupled to electronics module 55 and electronics module 55 may control the linear actuator device. A linear variable differential transformer (LVDT) may be employed, as an alternative to scale 35, to register displacement relative to the datum frame and thereby determine transverse dimension 12, and the LVDT may be coupled to electronics module 55. Alternatively, transverse dimension 12 may be determined using a digital electronic micrometer with an electronic digital readout, which is available from The L.S. Starrett Company, Athol, Mass., USA, and the electronic digital readout may coupled to electronics module 55 by an electrical lead 53.

Transit times may be determined at a pulse repetition frequency appropriate to the fluid 8 and the tube 10, as described below. Transit time determinations may be carried out at times when specific path lengths or changes in path lengths are reached, or at times or time intervals that are essentially independent of changes in transverse dimension 12. In other words, transit time determinations may be carried out independent of the rate or amount of deformation of segment 14, and furthermore, transit time determinations may be carried out without regard to the specific means for applying force that is used to change transverse dimension 12. A large number of value pairs for transverse dimension 12 and transit time may be transmitted to electronics module 55. Electronics module 55 may include memory means and processor means for processing the value pairs to determine a characteristic such as sound speed.

Embodiments described herein pertain to reversible changes in a transverse dimension of a segment 14 of a tube 10. If a tensile or compressive force or stress is applied to an elastic material, causing a strain in the material, and if the stress is small, then the ratio of stress to strain is a constant, as stated in Hooke's law. A graph of strain versus stress will be linear for small values of stress, and this linear region of the stress-strain graph is called the linear-elastic region. In the linear-elastic region, when the applied force or stress is reduced, the material will return to its original shape; in other words, the change in dimension is reversible. As used herein, a reversible change in a transverse dimension of a segment 14 of a tube 10 made of a particular material means that the applied force or stress is within the linear-elastic region for that material. The phrases "reversible deformation of tube 10" and "tube 10 is reversibly deformed" are used herein to mean a reversible change in a transverse dimension of a segment 14 of a tube 10. For resilient tube materials, it may be advantageous to change transverse dimension 12 by at most 10 to 25 percent, while for stiffer materials such thin walled stainless steel the maximum reversible deformation may correspond to a change in transverse dimension 12 of only a few percent. In FIGS. 2A-F, transverse dimension 12 measures about 28 mm, 25 mm, and 22 mm in FIGS. 2B, 2D, and 2F, respectively. Compared to FIG. 2B, transverse dimension 12 is reduced by 11 percent in FIG. 2D and reduced by 21 percent in FIG. 2F.

If tube 10 is of a rubbery or soft, resilient consistency, then the return to its original dimensions may be aided by positive pressure of the fluid 8 within tube 10. If the pressure within tube 10 is negative, e.g. lower than ambient atmospheric pressure, it is advisable to compress segment 14 to only a moderate extent, and to provide lateral support to prevent excessive sideways bulging as transverse dimension 12 is reduced. Fluid 8 may be flowing, and it may be advantageous not to restrict the flow much, even during brief periods of measurement. In such a situation, the flow rate may be monitored independently, for example by ultrasonic means, to ensure that deformation of tube 10 does not excessively reduce the flow rate.

Tube 10 may be made of any material that is capable of being reversibly changed in a dimension and that is suitable for transmission of an ultrasonic signal. Usable materials include metals, metal alloys, plastics including fluoropolymers and leak-proof foam such as DuPont Styrofoam® expanded polystyrene or syntactic foam, composites, ordinary rubber, and silicone rubber. For example, tube 10 may be soft biomedical tubing made of medical grade silicone rubber, tetrafluoroethylene (TEFLON), PEEK (a polymer of oxy-1,4-phenylenoeoxy-1,4-phenylene-carbonyl-1,4-phenylene). In semiconductor processing, for example, tube 10 may be made of a plastic such as perfluoroalkoxy fluorocarbon (PFA) or fluoroethylene-propylene (FEP) or a metal such as type 316SS stainless steel. Brittle materials such as glass, graphite, or ceramics are unlikely to be advantageous for use in embodiments described herein. Transducers 51 may be located external to tube wall 11, as depicted in, for example, FIGS. 2A-F. If tube 10 is made of metal, transmission of an ultrasonic signal from one external transducer 51 to another external transducer 51 may not be practical unless fluid 8 is a liquid, or a gas at high pressure, preferably above six bar for air, and perhaps even higher pressure for a gas or gas mixture of average molecular weight less than about 20, or for a gas or gas mixture having a high attenuation at the selected ultrasonic interrogation frequency.

Embodiments described herein are capable of determining fluid sound speed even for a tube 10 having a fairly small transverse dimension 12, such as a tube 10 several millimeters in diameter. Sound speed determination may be feasible for an even smaller tube 10 using a very small transducer 51 at a high ultrasonic interrogation frequency. As noted above in connection with FIG. 2D and FIG. 2F, the path length within tube wall 11 is assumed to be the same for path 16 and path 17; in other words, the thickness of tube wall 11 is assumed to remain essentially the same when tube 10 is reversibly deformed. If tube 10 were compressed to an extreme degree, the resulting strain might cause thinning of one region of tube wall 11 or thickening of another region of tube wall 11. If tube wall 11 becomes thinner, intra-wall transit time decreases; conversely, if tube wall 11 becomes thicker, intra-wall transit time increases. The assumption of an unchanged thickness for tube wall 11 is expected to be valid for a tube wall 11 made of a soft material where the transverse dimension 12 changes by 10 to 20 percent or less compared to the original transverse dimension 12 with no applied force. For a tube wall 11 made of a harder material, such as type 316SS stainless steel, a change in transverse dimension that is reversible, as described above, suffices for maintaining constant thickness of tube wall 11. For materials of intermediate hardness, transverse dimension changes of about 2 to 10 percent may be appropriate, depending upon the thickness of tube wall 11 and fluid pressure within tube 10, for maintaining an effectively constant wall thickness. Referring again to FIG. 3, determination of multiple value pairs (points) may reveal departures from linearity for a line passing through most of the points, and may indicate preferred and allowable limits for percent change in transverse dimension. Sound speed preferably is determined using value pairs (points) obtained from the linear region of the graph of FIG. 3. Known rules exist for disregarding, or eliminating from consideration, points that deviate too far from linearity, such that a meaningful best fit yields a slope that in turn yields an accurate determination of fluid sound speed.

Transducer 51 may be any suitable ultrasonic transducer such as, for example, a nondestructive testing (NDT) transducer available from Panametrics NDT (Olympus) of Waltham, Mass., USA. Transducer 51 may also be, for example, a capacitive microfabricated ultrasound transducer (CMUT) which is available from Siemens Medical Solutions USA, Inc., Malvern, Pa. 19355. The number and arrangement of transducers 51 may vary in different embodiments. The embodiment of FIGS. 1A-B and FIGS. 2A-F employs two transducers 51 for launching and receiving an ultrasonic signal along a path, using the through-transmission mode, as known in the art. An alternative embodiment may employ a single transducer 51 for launching and receiving an ultrasonic signal along a path, using the pulse-echo mode, as known in the art. An alternative embodiment may employ two or more transducers 51, with a single transducer for each of two or more paths. Yet another embodiment may employ a single transducer 51 per path on certain paths and two transducers 51 per path on other paths.

When transducer 51 is held against tube wall 11 by a force applying means such as spindle 33, this results in a "dry coupling" or "dry pressure coupling" that enables the ultrasonic signal to be launched and received effectively through tube wall 11, as is known in the art. Use of "dry pressure coupling" may be advantageous because it eliminates the need to use an oil or gel as an alternative means for coupling transducer 51 and tube wall 11. Transducers 51 are depicted with flat faces in FIGS. 1A-B and 2A-F. However, one or both faces, or wear plates attached thereto by means known in the art, may have a vee contour to facilitate centering tube 10 about axis AA of FIG. 1B. Ultrasonic signals may be launched and received using various techniques, as is known in the art. The through-transmission technique may be useful when two transducers 51 are used for a single path. The pulse-echo technique or mode may be useful when a single transducer 51 is used for a single path. Electronics module 55 may include means for separating conduit wall echoes from echoes across the fluid path, as is known in the art. By utilizing well known measuring modes, such as thickness gauges Modes 1, 2 and 3, available from Panametrics NDT, Waltham, Mass., wall transit time can be distinguished from fluid transit time.

FIGS. 4A and 4B are cross-sectional views of a portion of an apparatus and tube, the apparatus including a single transducer 51, in accordance with another embodiment. The embodiment of FIGS. 4A-B is similar to the embodiment of FIGS. 1A-B, except for the use of a single transducer 51, and includes a conventional micrometer 30 that includes an anvil 32 and a spindle 33. The single transducer 51 may be attached to anvil 32, as depicted in FIG. 4A, or transducer 51 may be attached to spindle 33 in another embodiment. Transducer 51 operates in pulse-echo mode: the ultrasonic signal propagates along a reflected path 16 that is depicted by a pair of arrows with opposite orientation in FIG. 4A. Transducer 51 launches an ultrasonic signal that propagates through tube wall 11 in a first wall region 22 adjacent transducer 51 and then propagates through fluid 8. The ultrasonic signal reflects from an inner surface 24 of a second wall region 23, propagates through fluid 8, propagates through tube wall 11 in first wall region 22, and is finally received at transducer 51. The transverse dimension 12 and the transit time of the ultrasonic signal along path 16 may be determined as described previously for the embodiment of FIGS. 1A-B and FIGS. 2A-F.

FIG. 4B is similar to FIG. 4A, except that in FIG. 4B spindle 33 has advanced, causing a reduction in transverse dimension 12. The path length for path 17 of FIG. 4B is smaller than the path length for path 16 of FIG. 4A. In this embodiment, the path length difference for paths 16 and 17 is substantially equal to twice the change in the transverse dimension 12 from FIG. 4A to FIG. 4B. The fluid sound speed may be determined, based on the path length difference and the transit time for path 16 and the transit time for path 17, in a manner similar to that described in connection with FIG. 3. The change in the transverse dimension 12 from FIG. 4A to FIG. 4B is multiplied by two, and the resulting value is divided by the transit time difference for paths 16 and 17, yielding the fluid sound speed. It is known in the art to use multiple traverses across a medium to increase the transit time and thereby improve fractional resolution of a transit time determination. Pulse-echo mode uses at least two traverses across the fluid, and in some circumstances may utilize four or six traverses, for example.

Use of a single transducer 51, as in the embodiment of FIGS. 4A and 4B, may be advantageous in terms of minimizing cost and complexity. Use of a single transducer 51 may reduce the size of the portion of apparatus 5 that fits around tube 10, and such a reduced size may be advantageous when tube 10 is located within a confined space such as the interior of a biomedical device. In an embodiment such as that of FIGS. 4A-B that uses the pulse-echo mode, the path lengths for paths 16 and 17 are not determined; rather, the path length difference between the two path lengths is determined. In contrast, in an embodiment such as that of FIGS. 2A-F that uses through-transmission, a path length may be determined directly from transverse dimension 12. In FIG. 2D, for example, the path length for path 16 is substantially equal to the transverse dimension 12. Thus, one can determine a characteristic such as sound speed based on information that includes the path lengths for the two paths depicted in FIGS. 2D and 2F and the transit times for the two paths.

Figure 7A:
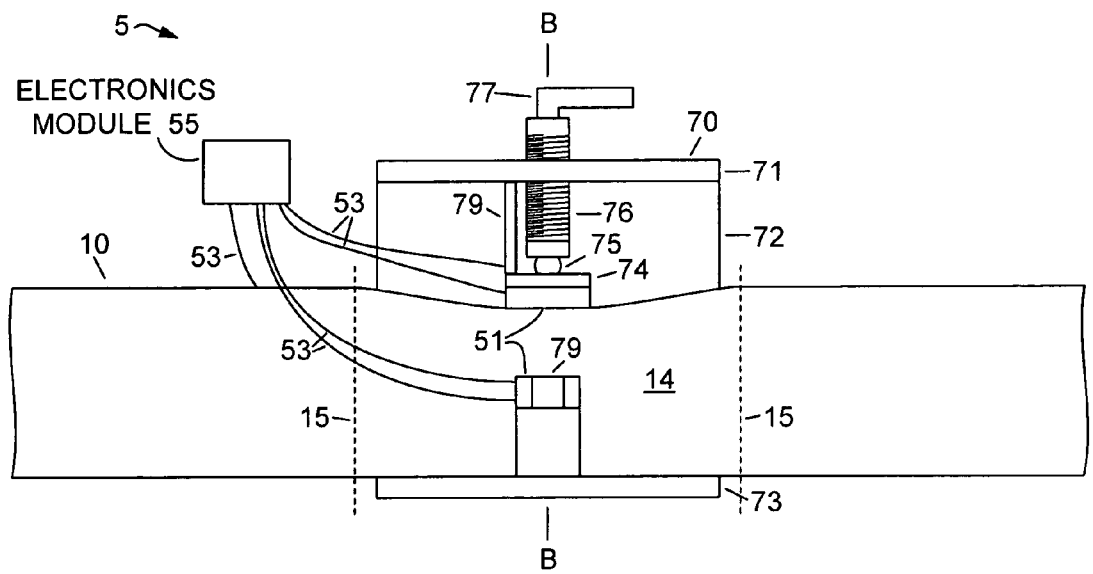
FIG. 7A is a side view of an apparatus for determining a characteristic of a fluid in a tube, in accordance with another embodiment; the apparatus is depicted prior to closing of a door.
Figure 7B:
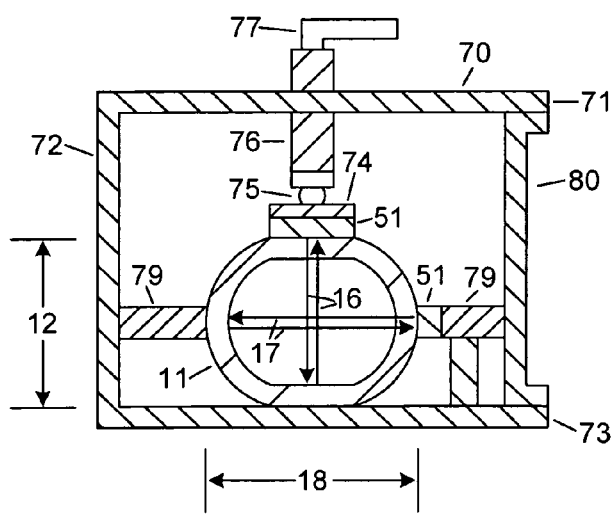
FIG. 7B is a cross-sectional view of the apparatus and tube of FIG. 7A, with the plane of section taken along line BB of FIG. 7A.

In some embodiments, it may be preferable that fluid 8 be homogeneous in composition and temperature; in other words, fluid 8 would not comprise stratified regions that differ in composition or temperature. Homogeneity may be achieved by flow, vibration, magnetic or mechanical stirring, or by other means known in the art. Homogeneity may be verified using two or more differential paths that are oriented at different angles relative to the tube wall, in order to sample multiple regions within the cross section of the fluid. For example, FIGS. 7A-B depict an embodiment with two paths 16 and 17 oriented orthogonal to one another; FIGS. 7A-B are described below.

If more than one transducer 51 is employed for launching and receiving signals along separate paths, electronics module 55 may include switching means to facilitate electronic switching among the separate paths, as is known in the art. Timing means in electronics module 55 preferably is accurate to plus or minus 1 nanosecond for ultrasonic pulses in the ultrasonic interrogation frequency range of about 1 to 10 MHz. Ultrasonic interrogation frequency is understood to mean the frequency of the ultrasonic wave that is interrogating the fluid, and therefore equals the number of ultrasound wave peaks per unit time for an ultrasonic signal. If the interrogating pulse contains only one or a few cycles, i.e. if the pulse is a tone burst, then the interrogation frequency may be taken as the center frequency of the spectrum of the pulse or burst. Pulse repetition frequency is understood to mean the number of ultrasonic signals launched per unit time. For embodiments described herein, and where fluid 8 is a liquid, the pulse repetition frequency may be in the kHz range, e.g. 1000 to 5000 Hz, and the ultrasonic interrogation frequency may be about 1 to 10 MHz. Where fluid 8 is a gas, the pulse repetition frequency may be 50 to 500 Hz and the ultrasonic interrogation frequency may be about 0.1 to 1 MHz. High pulse repetition frequencies may be facilitated if tube wall 11 or fluid 8 is inherently highly attenuative, or if tube 10 is adequately dampened by known means such as a band or patch made of silicone, soft rubber, or TEFLON applied external to tube wall 11.

It may be advantageous to ultrasonically interrogate two or more differential paths in a small time period such as 0.1 second or 0.01 second; this implies reversible deformation of tube 10 within a small time period. Extremely rapid deformation of tube 10 might cause heating of tube wall 11 by frictional or relaxation effects within the wall, and such heating could, via the thermoelastic effect, influence the intra-wall transit time of an ultrasonic signal 13. Monitoring the wall transit time provides a way to determine if tube wall 11 is heating. For the materials mentioned above, if the temperature of tube wall 11 increases, sound speed within the wall decreases, so the intra-wall transit time increases. As a numerical example of the thermoelastic effect in TEFLON, the longitudinal ultrasonic velocity (sound speed) at several temperatures is as follows: 25° C., 1400 m/s; 40° C., 1320 m/s; 80° C., 1220 m/s; 120° C., 1120 m/s. In 316SS the thermoelastic effect is much smaller. Fluid 8 within tube 10 may dissipate heat; if such dissipation occurs, monitoring intra-wall transit time for a few seconds while maintaining a fixed transverse dimension will reveal cooling by a decrease in wall transit time. If one considers the deformation process as inadvertently delivering energy to the wall, then rapid and repetitive deformations may tend to heat the wall more than deformations that are slow or well separated in time. One deformation, executed slowly, will cause negligible heating in most instances, particularly if fluid 8 is flowing and carries heat away from the segment in which sound speed is to be determined accurately. Maximum allowable deformation rates and repetition rates can be determined by calibration with empty tubes, and by monitoring the intra-wall transit time as a measure of wall temperature immediately after the tube reverses to its original unstressed dimensions.

FIG. 5A is a perspective view of a spacer 40 having two grooves 41 and 42 that differ in depth, the two grooves being oriented perpendicular to one another. Spacer 40 may be used with an elongate rectangular transducer 51 set into either groove 41 or groove 42. FIGS. 5B and 5C are side views of the spacer of FIG. 5A. In FIG. 5B the spacer is viewed from one end of groove 42, with an elongate rectangular transducer 51 set into groove 42. In FIG. 5C the spacer is viewed from one end of groove 41, with an elongate rectangular transducer 51 set into groove 41. Groove 42 is deeper than groove 41; a depth difference 43 is depicted in FIG. 5C.

Spacer 40 may be included in an apparatus similar to that of FIGS. 1A-B that includes a micrometer 30. Spacer 40 with depth difference 43 serves as part of the means for applying force to change transverse dimension 12 and also serves as a means of determining a path length difference derived from a change in transverse dimension 12. By using spacer 40, transverse dimension 12 may be changed by a predetermined amount such as 1 mm without reading scale 35. FIG. 5D is a cross-sectional view of a portion of an apparatus and tube, the apparatus including a spacer 40 adjacent a spindle 33, with a transducer 51 fitted into groove 42, in accordance with an embodiment. The embodiment of FIG. 5D is similar to the embodiment of FIG. 4A, except for the addition of spacer 40 and the repositioning of the single transducer 51.

Transducer 51 is initially set into groove 41, spindle 33 is advanced and locked in place, and a first ultrasonic signal is launched and received along a path having a first path length. Transducer 51 is then moved to groove 42 but without repositioning spindle 33, causing a change in transverse dimension 12, and a second ultrasonic signal is launched and received. The depth difference 43 equals the difference in transverse dimension 12. Fluid sound speed may be determined in a manner similar to that described in connection with FIGS. 4A and 4B. Spacer 40, with attached transducer 51, may alternatively be located adjacent anvil 32. FIG. 5E depicts another embodiment similar to that of FIG. 5D. Tube wall 11 sits within groove 42 or within an alternate groove 41 having a different depth. Repositioning spacer 40, so that tube wall 11 sits within groove 42 or within groove 41, causes a change in transverse dimension 12 and a change in path length.

Figure 6A:
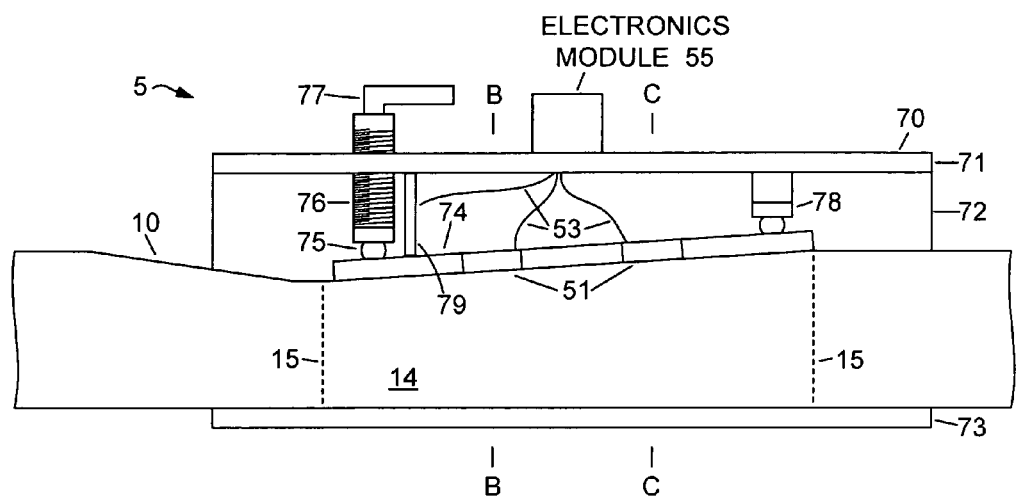
FIG. 6A is a side view of an apparatus for determining a characteristic of a fluid in a tube, in accordance with another embodiment.

FIG. 6A is a side view of an apparatus 5 for determining a characteristic of a fluid in a tube 10, in accordance with another embodiment. Apparatus 5 includes a datum frame 70 having a roof 71, a side 72, and a floor 73. Tube 10 rests upon floor 73. Segment 14 of tube 10 is delimited by segment boundaries 15. Force is applied to segment 14 by force means that include a threaded rod 76 mounted on datum frame 70, a swivel bearing 75, and an urging member 74. One end of urging member 74 is attached to roof 71 via a hinge 78. The other end of urging member 74 may be raised or lowered by retracting or advancing threaded rod 76 using lever 77. Two transducers 51 are held against tube 10 by urging member 74. A displacement indicator 79 registers the distance between roof 71 and urging member 74 in the vicinity of threaded rod 76. By geometry, one may determine the distance between roof 71 and each transducer 51. In an alternative embodiment, an individual displacement indicator 79 may be positioned directly above each transducer 51. Displacement indicator 79 may be, for example, a linear variable differential transformer (LVDT), which is available from Honeywell Sensotec, Columbus, Ohio, USA, a digital-output caliper available from Sears, or an optical displacement indicator, which is available from Nano-Trend, Taiwan, PRC. The two transducers 51 and displacement indicator 79 are coupled to electronics module 55 by electrical leads 53. In an alternative embodiment, force may be applied to variably deform segment 14 using a cam positioned between roof 71 and tube 10. The cam may be actuated in discrete steps or continuously, or the actuation sequence may be partly discrete and partly continuous. In discrete mode, the cam may be actuated through angles having discrete values at which cam motion temporarily ceases. In continuous mode, the cam may be actuated through continuously varying angles within predetermined limits.

Figure 6B:
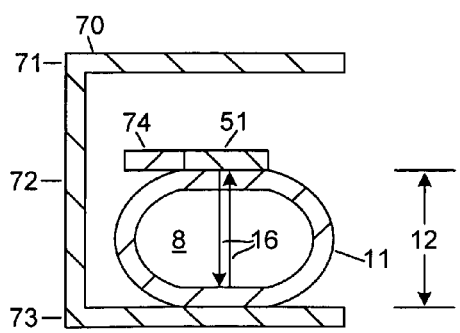
FIG. 6B is a cross-sectional view of the apparatus and tube of FIG. 6A, with the plane of section taken along line BB of FIG. 6A.
Figure 6C:
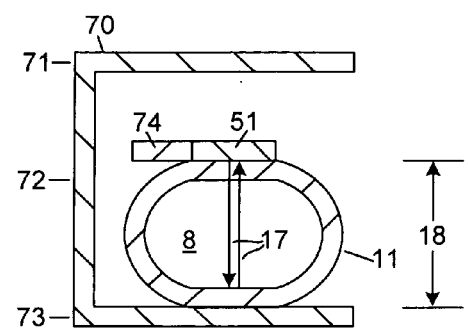
FIG. 6C is a cross-sectional view of the apparatus and tube of FIG. 6A, with the plane of section taken along line CC of FIG. 6A.

FIG. 6B is a cross-sectional view of the apparatus and tube of FIG. 6A, with the plane of section taken along line BB of FIG. 6A. FIG. 6C is a cross-sectional view of the apparatus and tube of FIG. 6A, with the plane of section taken along line CC of FIG. 6A. Deformation of segment 14 is greater in the region depicted in FIG. 6B compared to the region depicted in FIG. 6C. Transverse dimension 12 in FIG. 6B is smaller than transverse dimension 18 in FIG. 6C. Transverse dimensions 12 and 18 may be determined based on the thickness of transducers 51 and the distance between roof 71 and each transducer 51 and the distance between roof 71 and floor 73. Transducer 51 of FIG. 6B launches and receives an ultrasonic signal along reflected path 16. Transducer 51 of FIG. 6C launches and receives an ultrasonic signal along reflected path 17. Path 17 is longer than path 16; the path length difference between path 16 and path 17 is substantially equal to twice the difference between transverse dimension 12 and transverse dimension 18. Dividing the path length difference by the transit time difference for paths 16 and 17 yields the fluid sound speed. In another embodiment, additional differential paths may be employed by including additional transducers 51 held at additional positions by urging member 74.

FIG. 7A is a side view of an apparatus 5 for determining a characteristic of a fluid in a tube 10, in accordance with another embodiment; apparatus 5 is depicted prior to closing of a door. FIG. 7B is a cross-sectional view of apparatus 5 and tube 10 of FIG. 7A, with the plane of section taken along line BB of FIG. 7A, and with door 80 closed. Apparatus 5 includes a datum frame 70 having a roof 71, a side 72, and a floor 73. Tube 10 rests upon floor 73. Segment 14 of tube 10 is delimited by segment boundaries 15. Force is applied to segment 14 by force means that include a threaded rod 76 mounted on datum frame 70, a swivel bearing 75, and an urging member 74. Urging member 74 may be raised or lowered by retracting or advancing threaded rod 76 using lever 77. A displacement indicator 79 registers the distance between roof 71 and urging member 74 in the vicinity of threaded rod 76. A transducer 51 is held against tube 10 by urging member 74. An additional transducer 51 and two additional displacement indicators 79 are positioned lateral to tube 10. The two transducers 51 and the three displacement indicators 79 are coupled to electronics module 55 by electrical leads 53.

Two transverse dimensions 12 and 18 are indicated in FIG. 7B. Advancing threaded rod 76 causes a decrease in transverse dimension 12 and also causes an increase in transverse dimension 18. Retracting threaded rod 76 causes an increase in transverse dimension 12 and a decrease in transverse dimension 18. Transverse dimension 12 may be determined based on: the thickness of urging member 74 and adjacent transducer 51, the distance registered by displacement indicator 79 adjacent urging member 74, and the distance between roof 71 and floor 73. Transverse dimension 18 may be determined based on: the thickness of the transducer 51 that is positioned lateral to tube 10, the distances registered by the two displacement indicators 79 that are positioned lateral to tube 10, and the distance between side 72 and door 80.

Transverse dimension 12 in FIG. 7B is smaller than transverse dimension 18 in FIG. 7B. The transducer 51 adjacent urging member 74 launches and receives an ultrasonic signal in pulse-echo mode along reflected path 16. The transducer 51 positioned lateral to tube 10 launches and receives an ultrasonic signal in pulse-echo mode along reflected path 17. Path 17 is longer than path 16. The path length difference between path 16 and path 17 is substantially equal to twice the difference between transverse dimension 12 and transverse dimension 18. Dividing the path length difference by the transit time difference for paths 16 and 17 yields the fluid sound speed. In pulse-echo mode, the path length equals the dimension traversed multiplied by the number of traverses. In reflected path 16 or reflected path 17, the number of traverses is two, so the path length difference is substantially equal to twice the difference between transverse dimensions 12 and 18. For example, if the difference between transverse dimensions 12 and 18 were 1.5 mm, the path length difference would be 3 mm. If fluid 8 were water around room temperature, the transit time difference would be about 2 microseconds. Using an ultrasonic interrogation frequency of 1 MHz, the transit time difference is resolvable to about ±1 nanosecond.

Alternative embodiments may employ various other means for applying a force to reversibly deform tube 10, as alternatives to the force applying means described previously. For example, a cam, a hydraulically controlled force means, a vernier caliper, an adjustable torque wrench or a plumber's faucet puller might be employed. An alternative embodiment, similar to that depicted in FIGS. 7A-B, may employ pressurized gas to apply a force to tube 10. Such an embodiment may employ a rectangular enclosure having two roughly circular openings located in opposite end walls, with the enclosure divided into two sections along a horizontal plane that passes through the two circular openings. The edge of each circular opening may include a gasket. The enclosure may be installed around tube 10 with tube 10 passing through the two circular openings, and the two sections of the enclosure may be secured to one another. Pressurized gas may be introduced from a gas source, and a valve may be used to release gas and reduce pressure. Transducers 51 and displacement indicators 79 may be similar to those of FIGS. 7A-B. Two different gas pressures P1 and P2 may be applied, to yield different transverse dimensions 12. Alternatively, the gas pressure may be increased gradually from P1 to P2 during a period of, for example, 60 seconds; during the same time period, numerous value pairs for transverse dimension 12 and transit time may be obtained.

Values for transverse dimension 12 for individual paths, and path length differences for differential paths, may be registered electronically and transmitted to electronics module 55 for use in determining a characteristic such as sound speed. For example, displacement indicators 79 of FIGS. 6A and 7A-B are coupled to electronics module 55 by electrical leads 53. As described in connection with FIGS. 1A-B and 2A-F, scale 35 of micrometer 30 may be used for determining transverse dimension 12 for a segment 14. In another embodiment, micrometer 30 may be a digital electronic micrometer with an electronic digital readout, which is available from The L.S. Starrett Company, Athol, Mass., USA, and the electronic digital readout may be coupled to electronics module 55 by an electrical lead 53.

The differential paths may be oriented in various ways relative to one another in various embodiments. Differential paths may be colinear, parallel, or orthogonal (perpendicular) to one another. Alternatively, one path may be oriented oblique to another path, although oblique orientation results in a different intra-wall path length for the two paths; for most accurate results, corrections for the intra-wall path length difference may be applied. FIGS. 2A-F and FIGS. 4A-B depict embodiments that employ colinear paths. FIGS. 6A-C depict an embodiment that employs parallel paths. FIG. 7A-B depicts an embodiment that employs orthogonal paths. The differential paths may be oriented orthogonal to tube wall 11, as depicted in FIGS. 1-7, or may be oriented at a different angle with respect to tube wall 11. In the embodiment of FIG. 6A-C, for example, paths 16 and 17 are oriented orthogonal to tube wall 11 and are also oriented approximately but not completely parallel to lines BB and CC of FIG. 6A. In an alternative embodiment, paths 16 and 17 could be oriented oblique to tube wall 11.

Figure 8:
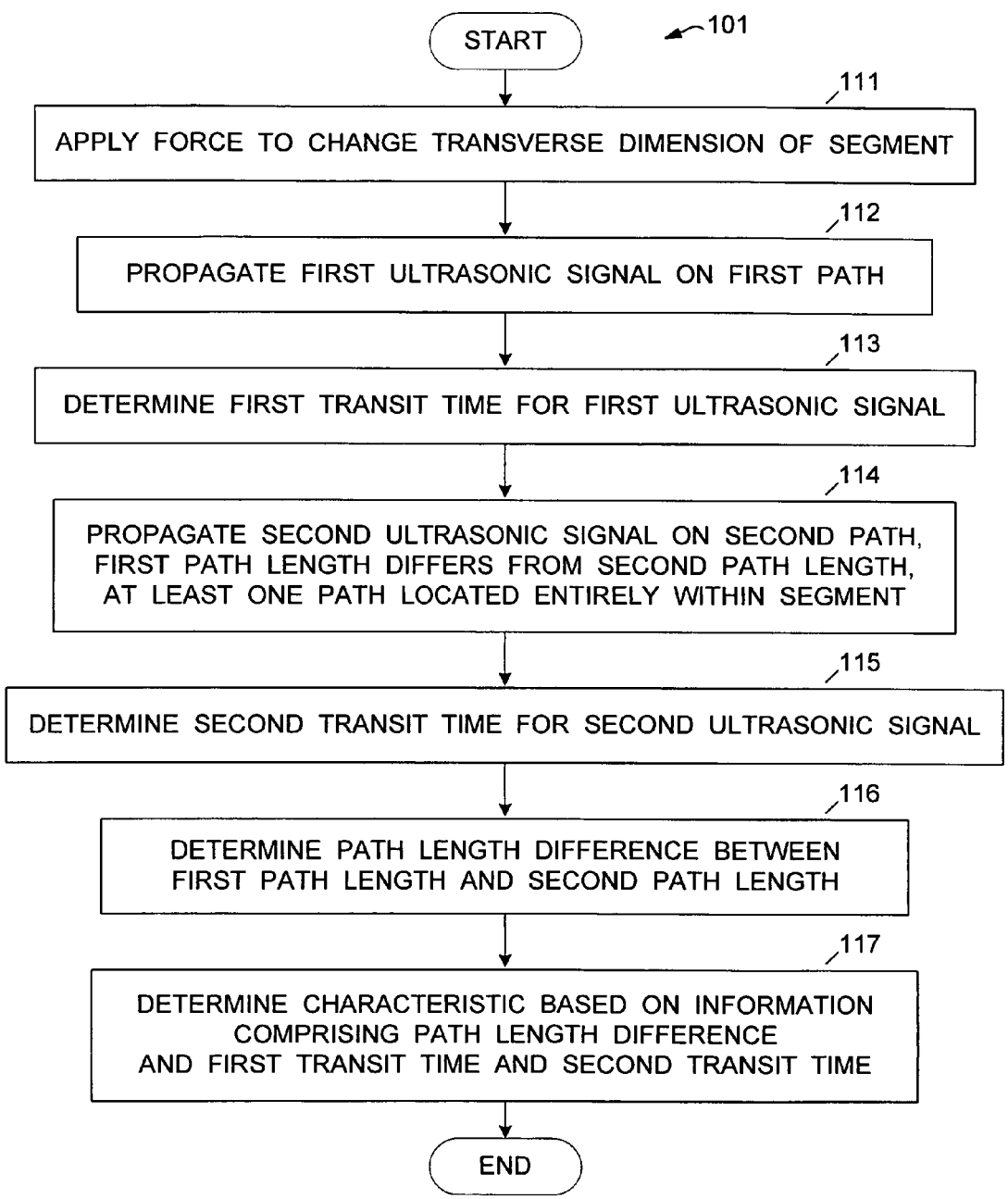
FIG. 8 is a simplified flowchart that depicts a method 101 for determining a characteristic of a fluid in a tube, in accordance with an embodiment.

FIG. 8 is a simplified flowchart that depicts a method 101 for determining a characteristic of a fluid in a tube, in accordance with an embodiment. Initially (step 111), a force is applied to cause a change in a transverse dimension of a segment of the tube. The deformation of the segment may create several differential paths, such as the parallel paths of the embodiment of FIGS. 6A-C, or the orthogonal paths of the embodiment of FIGS. 7A-B. In method 101, the differential paths are interrogated sequentially. A first ultrasonic signal is propagated along a first path (step 112), and a first transit time is determined for the first ultrasonic signal (step 113). A second ultrasonic signal is propagated along a second path (step 114); the first path length differs from the second path length and at least one of the first path and the second path is located entirely within the segment. A second transit time is determined for the second ultrasonic signal (step 115). A path length difference between the first path length and the second path length is determined (step 116). A characteristic such as sound speed is determined based on the path length difference and the first transit time and the second transit time (step 117).

Figure 9:
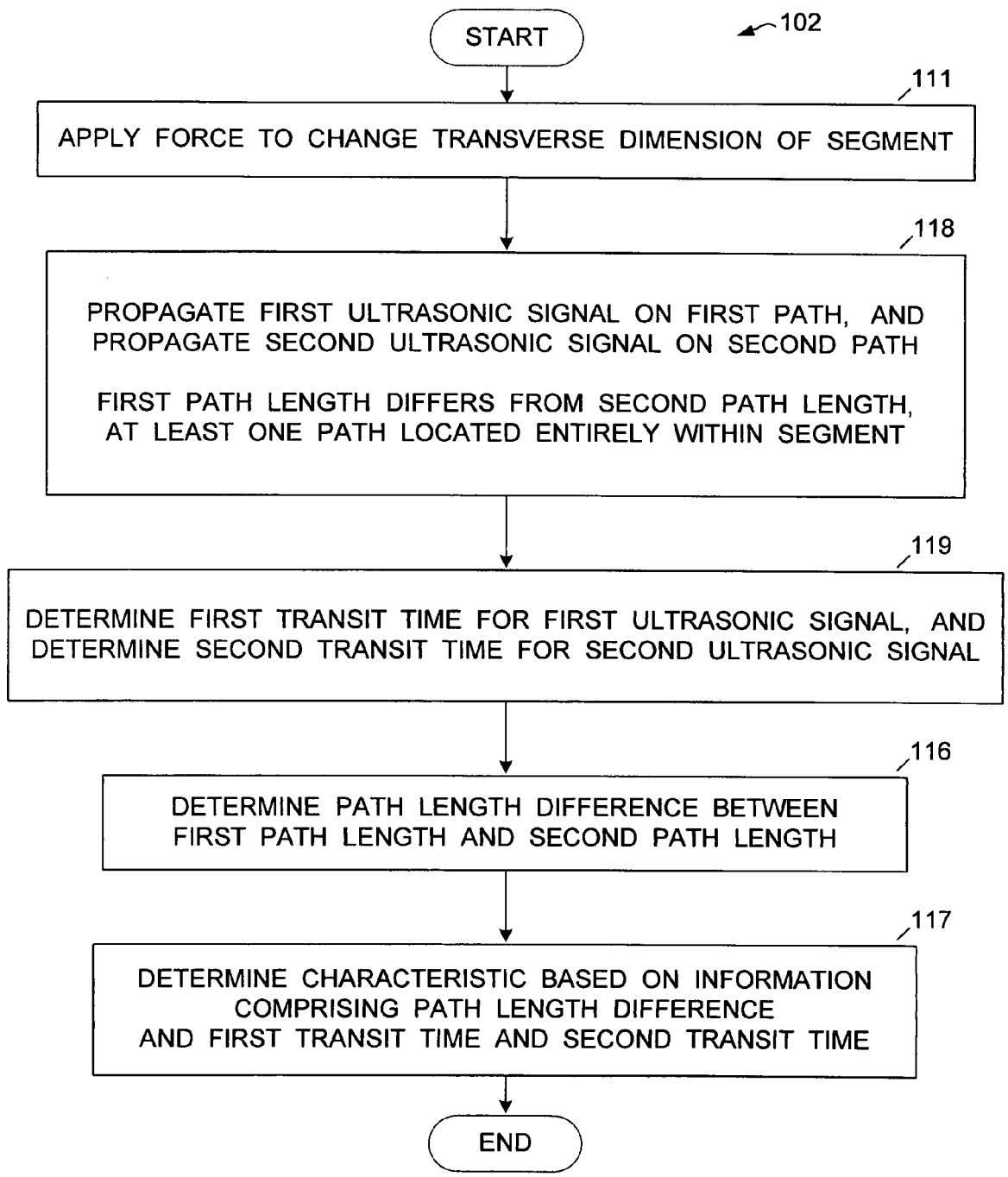
FIG. 9 is a simplified flowchart that depicts a method 102 for determining a characteristic of a fluid in a tube, in accordance with an embodiment.

FIG. 9 is a simplified flowchart that depicts a method 102 for determining a characteristic of a fluid in a tube, in accordance with an embodiment. Method 102 is similar to method 101 except that the differential paths are interrogated simultaneously rather than sequentially. Initially (step 111), a force is applied to cause a change in a transverse dimension of a segment of the tube. The deformation of the segment may create several differential paths, such as the parallel paths of the embodiment of FIGS. 6A-C, or the orthogonal paths of the embodiment of FIGS. 7A-B. A first ultrasonic signal is propagated along a first path and a second ultrasonic signal is propagated along a second path at substantially the same time (step 118); the first path length differs from the second path length and at least one of the first path and the second path is located entirely within the segment. A first transit time is determined for the first ultrasonic signal and a second transit time is determined for the second ultrasonic signal (step 119). A path length difference is determined (step 116) and a characteristic is determined (step 117) as described for method 101.

Figure 10:
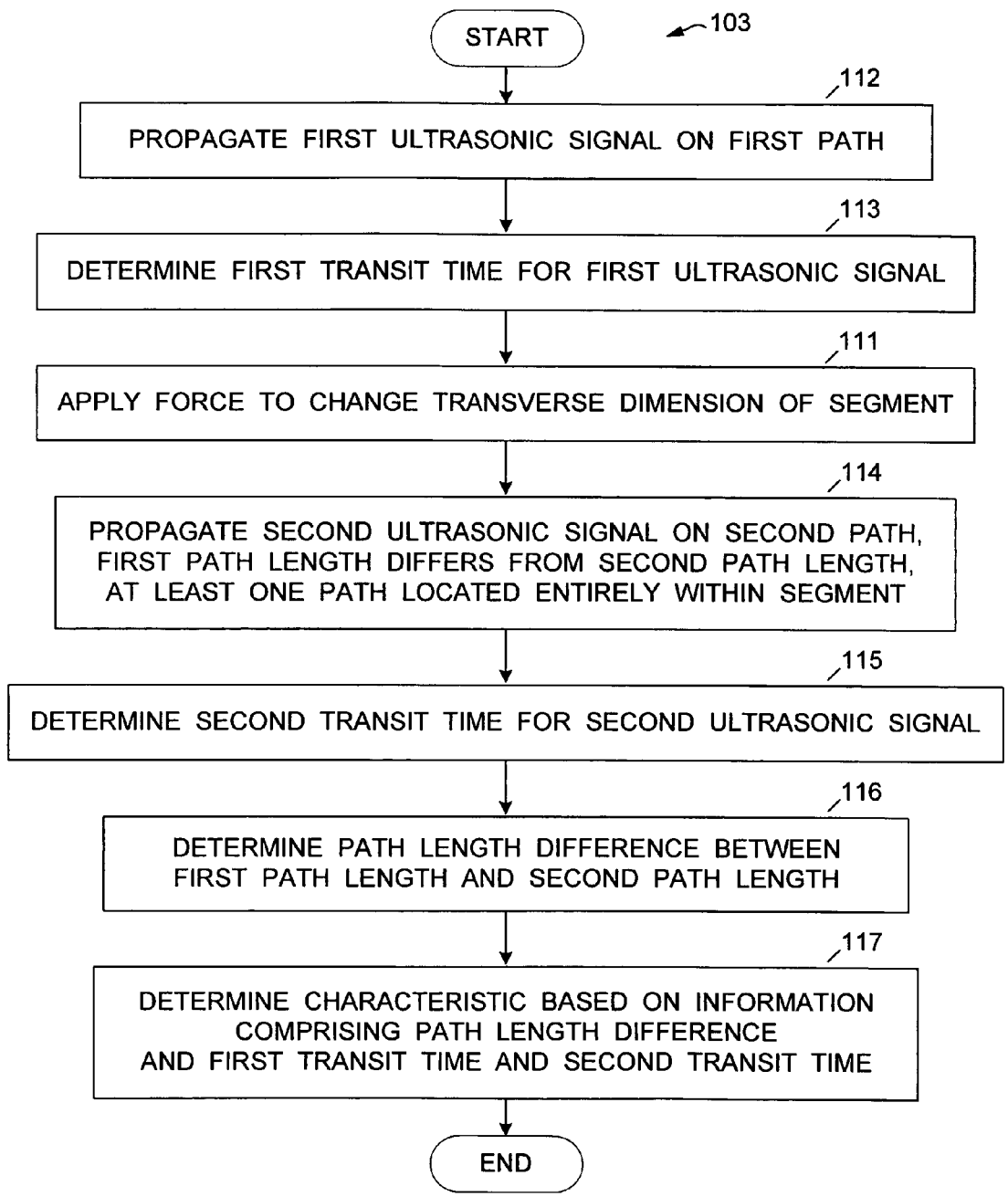
FIG. 10 is a simplified flowchart that depicts a method 103 for determining a characteristic of a fluid in a tube, in accordance with an embodiment.

FIG. 10 is a simplified flowchart that depicts a method 103 for determining a characteristic of a fluid in a tube, in accordance with an embodiment. Method 103 differs from methods 101 and 102 because the interrogation of a first path precedes the application of force that changes a transverse dimension of a segment. Method 103 may be used for colinear differential paths, such as the colinear paths of the embodiments of FIGS. 2A-F or 4A-B. In method 103, the differential paths are interrogated sequentially. A first ultrasonic signal is propagated along a first path (step 112), and a first transit time is determined for the first ultrasonic signal (step 113). A force is applied to cause a change in a transverse dimension of a segment of the tube (step 111). A second ultrasonic signal is propagated along a second path (step 114); the first path length differs from the second path length and at least one of the first path and the second path is located entirely within the segment. A second transit time is determined for the second ultrasonic signal (step 115). A path length difference between the first path length and the second path length is determined (step 116). A characteristic such as sound speed is determined based on the path length difference and the first transit time and the second transit time (step 117).

In methods 101 and 103, the differential paths are interrogated sequentially; in other words, ultrasonic signals are launched along differential paths at different times. In method 102, the differential paths are interrogated simultaneously. Simultaneous interrogation may be advantageous, as simultaneous interrogation may avoid errors due to changing conditions and may yield information about transient phenomena and process dynamics.

Figure 11:
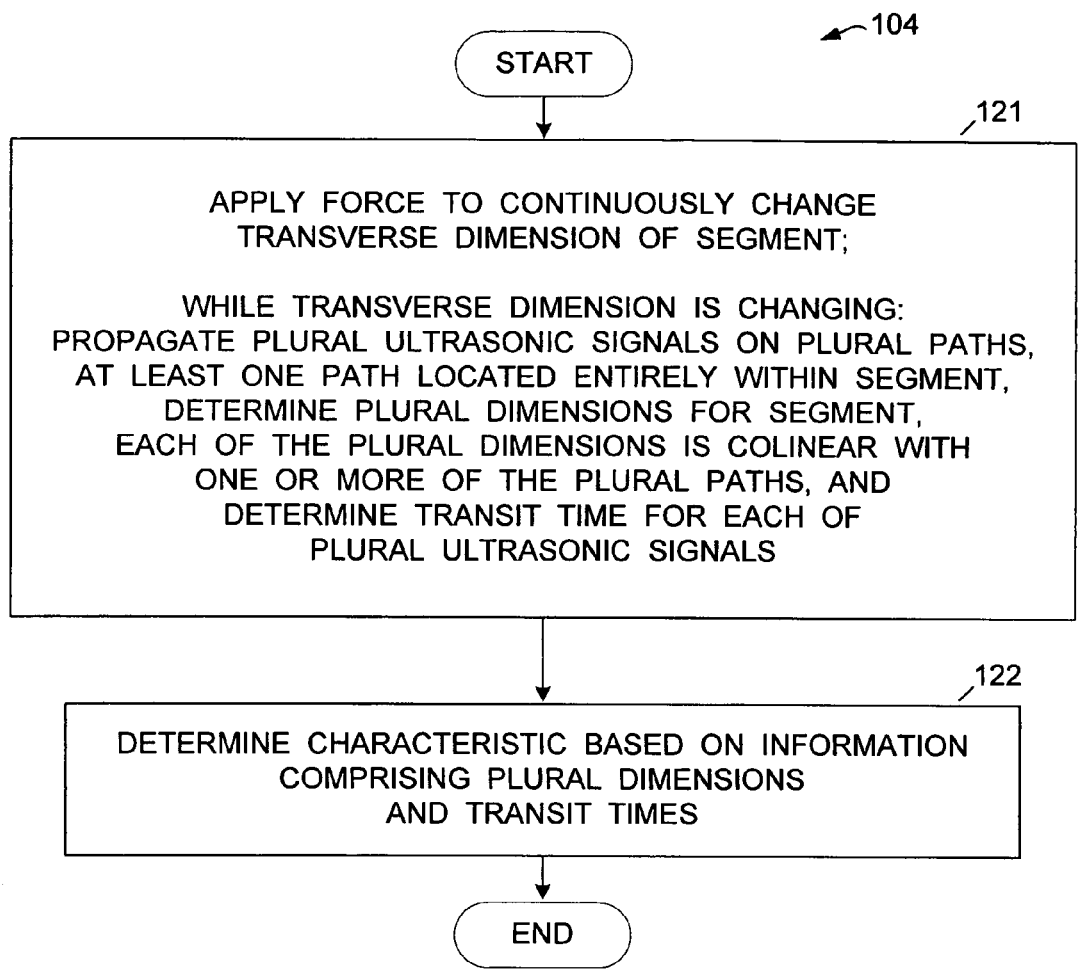
FIG. 11 is a simplified flowchart that depicts a method 104 for determining a characteristic of a fluid in a tube, in accordance with an embodiment.

FIG. 11 is a simplified flowchart that depicts a method 104 for determining a characteristic of a fluid in a tube, in accordance with an embodiment. In step 121, a transverse dimension of a segment of a tube changes continuously in response to an applied force. While the transverse dimension is changing, plural ultrasonic signals propagate on plural paths. Ultrasonic signals may be launched on differential paths simultaneously, as in method 102, or sequentially, as in methods 101 and 103. One or more of the paths is located entirely within the segment. The instantaneous dimension of the segment may be determined repeatedly, yielding plural dimensions; the dimension determined is colinear with one or more of the plural paths. For example, a dimension colinear with path 16 of FIG. 7B, and of length equal to transverse dimension 18 of FIG. 7B, may be determined as described in connection with FIG. 7B using lateral displacement indicators 79. The instantaneous value for a single dimension may be recorded repeatedly, or instantaneous values may be recorded repeatedly for several dimensions such as transverse dimensions 12 and 18 of FIG. 7B. A transit time is determined for two or more of the plural ultrasonic signals; for example, the transit time may be determined for each of the plural ultrasonic signals. In step 122, a characteristic is determined based on information comprising the plural dimensions and the transit times. As represented graphically in FIG. 3, information about transit times and segment dimensions may be used to determine sound speed; sound speed in FIG. 3 corresponds to the slope of the line passing through points 63-66.

Those of skill in the art will understand that an embodiment may combine: 1) any of various means for applying force; 2) any of various arrangements and numbers of transducers; 3) any of various means for determining a path length difference; 4) sequential or simultaneous launching of ultrasonic signals. The particular combination chosen for a particular embodiment may depend upon the nature of the tube 10 and fluid 8 of interest and the setting within which the tube 10 is located.

Determination of fluid sound speed for two or more differential paths may facilitate verification and validation of the fluid sound speed, as is known in the art. Linearity, homogeneity and consistency of data may be evaluated using sound speed determined for differential paths. Monitoring of ultrasonic signal amplitude for differential paths may help to evaluate sound speed determinations as well as to determine the attenuation coefficient of the fluid. If sound speed is determined for a fluid having no molecular absorption mechanisms active at the ultrasonic interrogation frequency employed and having no resonant scatterers such as bubbles, then in tests at two or more frequencies, sound speed should be constant, independent of frequency, while the attenuation coefficient is expected to increase in proportion to the square of frequency, as is known in the art. For increased accuracy, determinations of sound speed and of attenuation coefficient may be corrected for tube wall effects and for diffraction, as is known in the art. If the tube 10 of interest is of an industry-standard type, apparatus 5 may be calibrated using a separate tube 10 of the same industry-standard type, and using a pure, well-characterized fluid that is similar in composition to the fluid 8 of interest, at a known temperature.

Although we have described in detail various embodiments, other embodiments and modifications will be apparent to those of skill in the art in light of this text and accompanying drawings. The following claims are intended to include all such embodiments, modifications and equivalents.

What is claimed is:

1. An apparatus for determining a characteristic of a fluid in a tube, the tube including a tube wall, the tube wall including a first wall region and a second wall region, the apparatus comprising:
   (a) means for applying a force to cause a change in a transverse dimension of a segment of the tube, wherein the change in the transverse dimension is reversible; and
   (b) means for launching and receiving ultrasonic signals, wherein the means for launching and receiving ultrasonic signals comprises a single transducer, wherein a first ultrasonic signal propagates along a first path through the tube, the first path having a first path length, and a second ultrasonic signal propagates along a second path through the tube, the second path having a second path length, and wherein the first path length differs from the second path length and at least one of the first path and the second path is located entirely within the segment;

wherein the first path and the second path are colinear; wherein the first path is orthogonal to the tube wall and the second path is orthogonal to the tube wall;

wherein the first wall region is adjacent the single transducer; wherein each of the first ultrasonic signal and the second ultrasonic signal propagates through the tube wall in the first wall region and reflects from an inner surface of the second wall region.

2. The apparatus of claim 1, wherein the means for applying a force comprises a micrometer spindle and a micrometer anvil.

3. The apparatus of claim 1, wherein the means for applying a force comprises a threaded rod and a datum frame.

4. The apparatus of claim 1, further comprising means for determining a path length difference between the first path length and the second path length.

5. The apparatus of claim 4, wherein the means for determining a path length difference comprises a micrometer scale.

6. The apparatus of claim 4, wherein the means for determining a path length difference comprises a spacer having a first groove and a second groove, wherein a first depth for the first groove differs from a second depth for the second groove.

7. The apparatus of claim 4, wherein the means for determining a path length difference comprises a linear variable differential transformer (LVDT).

8. The apparatus of claim 4, wherein the characteristic is determined based on information comprising the path length difference and a first transit time for the first ultrasonic signal and a second transit time for the second ultrasonic signal.

9. The apparatus of claim 1, wherein the characteristic is determined based on information comprising the first path length and the second path length and a first transit time for the first ultrasonic signal and a second transit time for the second ultrasonic signal.

* * * * *